United States Patent [19]
Ream

[11] Patent Number: 5,957,941
[45] Date of Patent: *Sep. 28, 1999

[54] CATHETER SYSTEM AND DRIVE ASSEMBLY THEREOF

[75] Inventor: John H. Ream, San Jose, Calif.

[73] Assignee: Boston Scientific Corporation, Natick, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/721,433

[22] Filed: Sep. 27, 1996

[51] Int. Cl.$^6$ ..................................................... A61B 17/22
[52] U.S. Cl. .............................. 606/159; 606/2; 606/32; 600/443
[58] Field of Search ............... 604/95, 159; 128/DIG. 1; 606/1, 108, 159, 2, 32; 600/443

[56] References Cited

U.S. PATENT DOCUMENTS

| | | |
|---|---|---|
| 4,593,699 | 6/1986 | Poncy et al. . |
| 4,708,125 | 11/1987 | Miketi et al. . |
| 4,771,774 | 9/1988 | Simpson et al. . |
| 4,794,931 | 1/1989 | Yock . |
| 4,802,487 | 2/1989 | Martin et al. . |
| 4,841,977 | 6/1989 | Griffith et al. . |
| 4,917,097 | 4/1990 | Proudian et al. . |
| 5,000,185 | 3/1991 | Yock . |
| 5,048,529 | 9/1991 | Blumenthal . |
| 5,105,819 | 4/1992 | Wollschläger et al. . |
| 5,107,844 | 4/1992 | Kami et al. . |
| 5,125,410 | 6/1992 | Misono et al. . |
| 5,178,148 | 1/1993 | Lacoste et al. . |
| 5,203,338 | 4/1993 | Jang . |
| 5,211,176 | 5/1993 | Ishiguro et al. . |
| 5,259,732 | 11/1993 | Stern ................................. 128/DIG. 1 |
| 5,318,576 | 6/1994 | Plassche, Jr. et al. . |
| 5,321,501 | 6/1994 | Swanson et al. . |
| 5,366,464 | 11/1994 | Belknap . |
| 5,373,849 | 12/1994 | Maroney et al. . |
| 5,431,645 | 7/1995 | Smith et al. ................................. 606/1 |
| 5,485,846 | 1/1996 | Webler et al. . |
| 5,497,776 | 3/1996 | Yamakazi et al. . |
| 5,545,140 | 8/1996 | Conen et al. ....................... 128/DIG. 1 |
| 5,551,432 | 9/1996 | Iezzi . |
| 5,571,114 | 11/1996 | Devanaboyina ........................ 606/108 |

FOREIGN PATENT DOCUMENTS

| | | |
|---|---|---|
| 0244058 | 11/1987 | European Pat. Off. . |
| 0266858 | 5/1988 | European Pat. Off. . |
| 0626152 | 11/1994 | European Pat. Off. . |
| 2543817 | 10/1984 | France . |
| 4344312 | 7/1994 | Germany . |
| 90/01300 | 2/1990 | WIPO . |
| 91/15154 | 10/1991 | WIPO . |
| 92/19930 | 11/1992 | WIPO . |
| 93/16642 | 9/1993 | WIPO . |
| 94/00052 | 1/1994 | WIPO . |
| 94/11038 | 5/1994 | WIPO . |
| WO 94/00052 | 6/1994 | WIPO . |
| 97/32182 | 9/1997 | WIPO . |

OTHER PUBLICATIONS

Brochure: ClearView Ultra™ System / UltraCross™ Catheters (in Existence at least as of Sep. 26, 1996).

Jerome H. Siegel, MD et al., *Endoscopic Retrograde Cholangiopancreatography, Technique, Diagnosis, and Therapy*, pp. 5 and 400, Raven Press, New York.

Joseph E. Geenen, MD et al., *Techniques in Therapeutic Endoscopy*, Second Edition, pp. 1.14, 3.6, 7.4, 8.20, and 10.7, Gower Medical Publishing, New York:London.

*Primary Examiner*—Glenn K. Dawson
*Attorney, Agent, or Firm*—Townsend and Townsend and Crew LLP

[57] ABSTRACT

A system (2) includes broadly a catheter assembly (6) and a drive assembly (4). The catheter assembly includes a hollow sheath (20) housing a connecting element, typically a drive cable (22), with an operative element, such as a transducer (24), towards its distal end (26). The drive assembly is adapted to move the connecting element longitudinally within the hollow sheath. The drive assembly includes a main body (8) to which a proximal assembly, such as a rotary drive assembly (16), connected to the proximal end (28) of the connecting element, is mounted for longitudinal movement along the main body. The main body also has an anchor element (32) which is used to secure the sheath to the main body. A longitudinal drive motor (40) is carried by the main body and drives the proximal assembly along the main body.

35 Claims, 6 Drawing Sheets

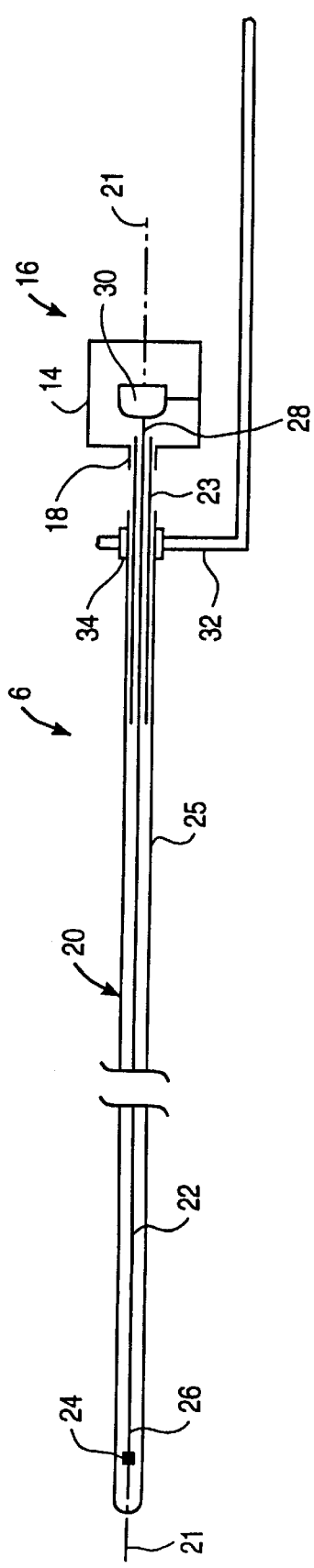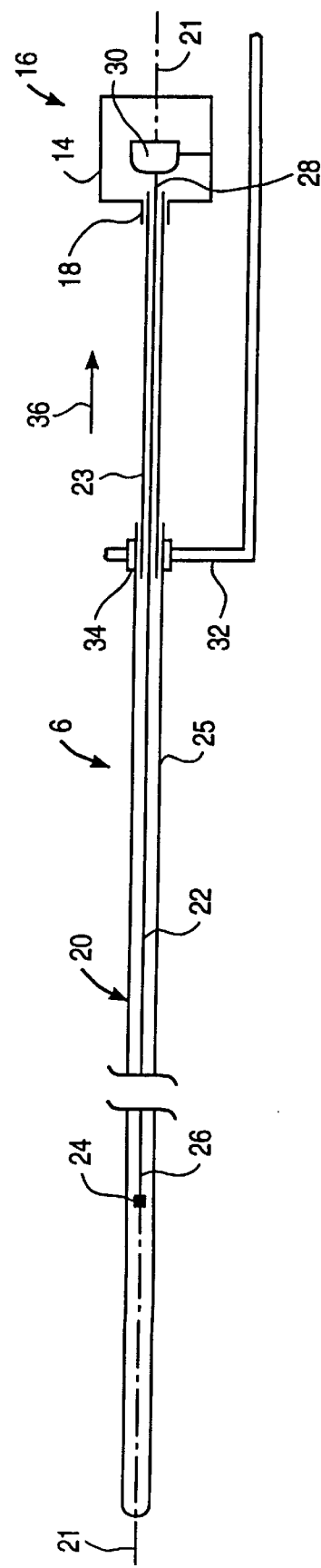
FIG. 3
FIG. 3A

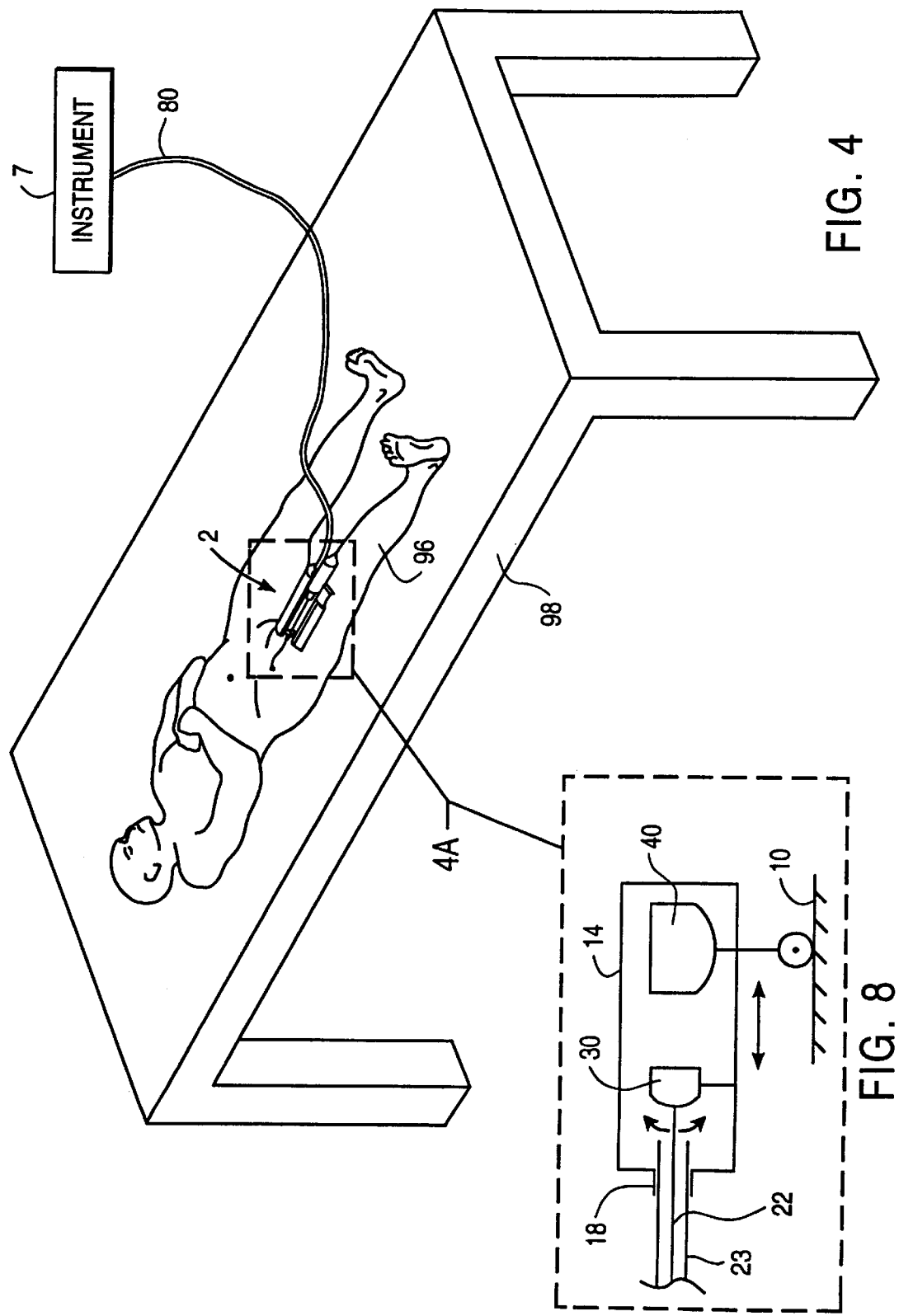

ized regions of a blood vessel, stenosis, or narrowing of the vascular channel, occurs. Blood flow is restricted and the person's health is at serious risk.

CATHETER SYSTEM AND DRIVE ASSEMBLY THEREOF

BACKGROUND OF THE INVENTION

The present invention relates generally to intraluminal imaging. More particularly, a medical imaging system is provided which permits the controlled longitudinal movement of an operative element, such as a rotatable transducer.

Arteriosclerosis, also known as atherosclerosis, is a common human ailment arising from the deposition of fatty-like substances, referred to as atheromas or plaque, on the walls of blood vessels. Such deposits occur in both peripheral blood vessels which feed the limbs of the body and the coronary vessels which feed the heart. When the deposits accumulate in localized regions of a blood vessel, stenosis, or narrowing of the vascular channel, occurs. Blood flow is restricted and the person's health is at serious risk.

Numerous approaches for reducing and removing such vascular deposits have been proposed, including balloon angioplasty where a balloon-tipped catheter is used to dilate a region of atheroma or other devices which are pushed or pulled across a lesion such as, atherectomy where a blade or cutting bit is used to sever and remove the atheroma, spark gap reduction in which an electrical spark burns through the plaque, laser angioplasty where laser energy is used to ablate at least a portion of the atheroma, and opening of vessels through the use of stents.

A major difficulty in using such devices is obtaining images of and information on the region of the blood vessel to be treated. To overcome this difficulty, several techniques have been proposed for intraluminal imaging of vascular vessels. Catheters incorporating ultrasonic transducers for imaging are disclosed in U.S. Pat. Nos. 4,794,931; 5,000,185; 5,049,130; and 5,024,234. These catheters scan in a plane normal to the catheter axis.

Generally deposits extend some longitudinal distance along the length of a vessel. To view different portions of the deposit a physician typically moves the transducer along the vessel, for example, by pushing or pulling the catheter.

Imaging using computer-assisted reconstruction algorithms enables physicians to view a representation of the patient's interior intravascular structures in two or three dimensions (i.e., so-called three-dimensional or longitudinal view reconstruction). In this connection, image reconstruction algorithms typically employ data-averaging techniques which assume that the intravascular structure between an adjacent pair of data samples will simply be an average of each such data sample. Thus, the algorithms use graphical "fill in" techniques to depict a section of a patient's vascular system under investigation. Of course, if data samples are not sufficiently closely spaced, then lesions and/or other vessel abnormalities may in fact remain undetected (i.e., since they might lie between a pair of data samples and thereby be "masked" by the image reconstruction algorithms mentioned previously).

Even with the most skilled physician, it is practically impossible manually to exercise constant rate longitudinal translation of an imaging device (which thereby provides for a precisely known separation distance between adjacent data samples). In addition, with manual translation, the physician must manipulate the translation device while observing the conventional two-dimensional sectional images. It is also difficult to manually exercise constant rate longitudinal translation of a work-performing element such an an artherectomy cutter or RF ablation element. This division of the physician's attention and difficulty in providing a sufficiently slow constant translation rate can result in some diagnostic information being missed. To minimize the risk that diagnostic information is missed, it is necessary to lengthen the imaging scan time which may be stressful to the patient.

U.S. Pat. No. 5,485,486 discloses an ultrasound imaging transducer which is capable of being translated longitudinally within a section of a patient's vascular system at a precise constant rate through the use of a longitudinal translation assembly. The longitudinal translation assembly causes the entire rotary drive assembly to provide the desired longitudinal movement of the transducer. Such an ability enables a series of precisely separated data samples to be obtained thereby minimizing (if not eliminating) distorted and/or inaccurate reconstructions of the ultrasonically scanned vessel section (i.e., since a greater number of more closely spaced data samples can reliably be obtained). Also, such an assembly can be operated in a "hands-off" manner which allows the physician to devote his or her attention entirely to the real-time images with the assurance that all sections of the vessel are displayed. While such a longitudinal translation assembly can work well, it is relatively large, bulky and heavy; it is expensive; and it is cumbersome to set up, in part because the rotary drive and longitudinal translation assemblies are wrapped in separate sterile drapes (plastic bags) for sterility.

SUMMARY OF THE INVENTION

The present invention is directed to a catheter system and drive assembly thereof which provides for controlled longitudinal movement of an operative element, such as an ultrasound transducer, within a catheter sheath. The assembly can be totally or almost totally self-contained, light in weight, and simple to set up and use.

The system includes broadly a catheter assembly and a longitudinal drive assembly. The catheter assembly comprises a hollow sheath housing an elongate, flexible connecting element with an operative element at or near its distal end, and a proximal end assembly at the proximal end of the connecting element. The connecting element can be a drive cable and the proximal end assembly can be a rotary driver for rotating the connecting element about the longitudinal axis. Lines to and from the operative element, such as power and signal lines, can extend along the connecting element. The drive assembly is adapted to move the connecting element longitudinally within the hollow sheath. In one embodiment this controlled longitudinal movement permits creation of three-dimensional vascular images.

The drive assembly includes a main body to which the proximal assembly is mounted for longitudinal movement along the main body. The main body includes an anchor element used to secure the sheath to the main body. A longitudinal drive motor is carried by the main body and drives a longitudinal drive train coupling the longitudinal drive motor and the proximal assembly.

In one embodiment the drive train includes a drive belt coupled to the proximal assembly by a user-actuated clutched coupler. The clutched coupler preferably includes a clutch handle which is supported by and moves with the proximal assembly. Using a clutch permits the user to disengage the proximal assembly from the longitudinal drive train at any position along the path of longitudinal movement of the proximal assembly permitting manual repositioning of the proximal assembly as desired.

The invention also preferably includes one or more adjustable legs extending from the main body to help support the system comfortably on, typically, the user's leg. The legs may be adjustable in their angular orientation, configuration and/or length. This aspect is important since it permits the physician to devote full attention to the operative procedure instead of splitting the physician's concentration due to a need to hold or stabilize the proximal assembly.

Another advantage of the invention is present when the proximal assembly is a rotary drive assembly. The rotary drive assembly need include only those components necessary to be moved along with the rotary drive motor. That is, the longitudinal drive motor, printed circuit board, control panel, and other such components need not be part of the rotary drive assembly so that the rotary drive assembly can be lighter in weight than would otherwise be necessary. The lighter weight means that the longitudinal drive motor can be smaller and the drive train can be simpler and lighter in construction than would be required if the rotary drive assembly contained additional components. This helps to reduce the weight and cost of the entire assembly.

A further advantage of the invention is that with the exception of the catheter assembly and a power/data cord (when needed), everything else is part of the drive assembly. This construction also helps to eliminate the practical problems associated with having parts of the drive assembly be external of the main housing or body, such as occurs when one or both of rotary drive and longitudinal drive motors are separate from the main body. For example, this permits a single sterile drape (typically a plastic bag) to be used to cover the entire drive assembly and a length of the any power/data cord. When the drive assembly provides for both rotary and longitudinal movement of the operative element, such drive assembly is as convenient to use as drive assemblies that only rotate the operative element but do not provide for controlled, automatic longitudinal movement for the operative element.

The disclosed embodiment shows the use of a rotatable ultrasound transducer as the operative element. Other image devices could be used as the operative element, such as phased array ultrasound transducers disclosed in U.S. Pat. Nos. 4,841,977 and 4,917,097, optical coherence tomography optical devices disclosed in U.S. Pat. No. 5,321,501 and other fiberoptic visualization devices. The operative element could also be a work-performing device, such as an artherectomy or other cutter device, a laser ablation device, an RF energy ablation device and other ablation energy devices. Likewise, in the disclosed embodiment the proximal end assembly is a rotary drive assembly. However, the invention can be practiced with proximal end assemblies which do not rotate the connecting element. For example proximal end assemblies designed for use with the above-mentioned operative elements could also be used.

Other features and advantages of the invention will appear from the following description in which the preferred embodiment has been set forth in detail in conjunction with the accompanying drawings.

BRIEF DESCRIPTION OF THE DRAWINGS

FIGS. 3 and 3A are simplified cross-sectional views of the system of FIGS. 1 and 1A illustrating the movement of the drive cable and transducer as the rotary drive assembly moves from the position of FIGS. 1 and 3 to the position of FIGS. 1A and 3A;

FIG. 4 shows the system of FIG. 1 in use on a patient resting on a support surface;

FIG. 8 is a schematic illustration showing the longitudinal drive motor of FIG. 2 housed within the rotary drive housing of FIG. 2.

DESCRIPTION OF A PREFERRED EMBODIMENT

Figure 1:
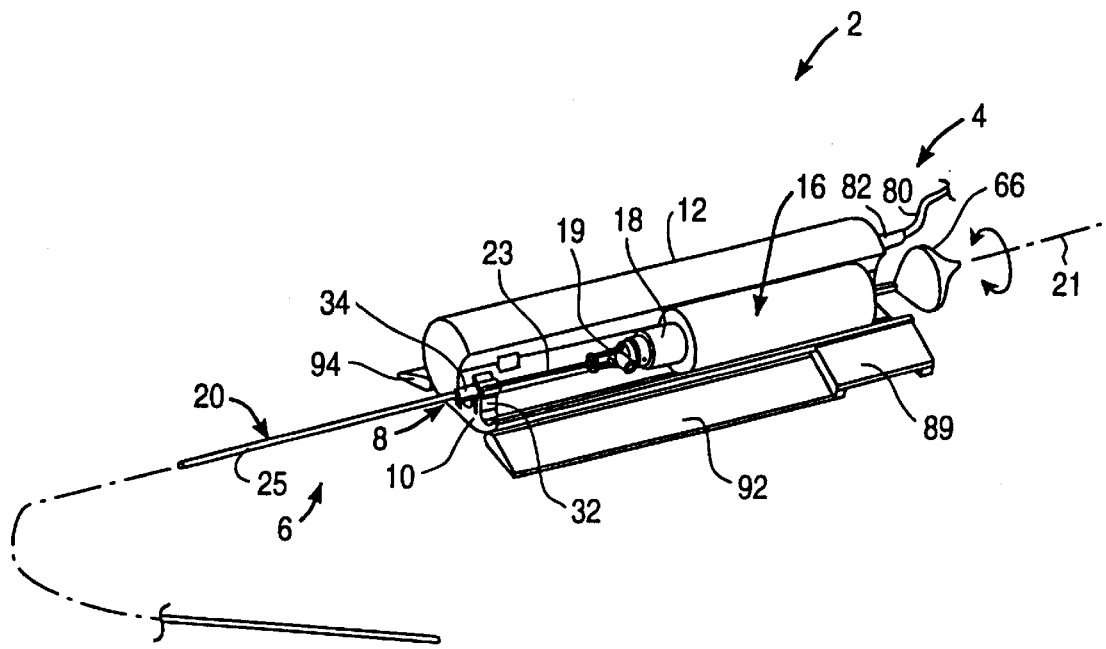
FIGS. 1 and 1A are overall views showing a vascular imaging system with the drive assembly in a partially collapsed condition in FIG. 1 and in an extended condition in FIG. 1A.
Figure 1A:
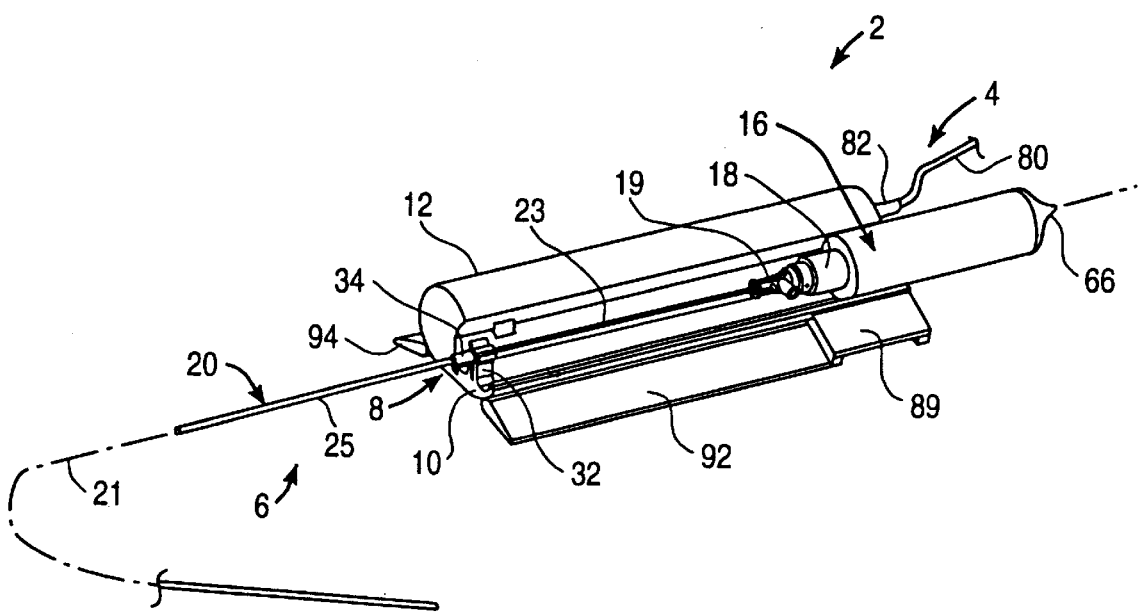
Figure 4A:
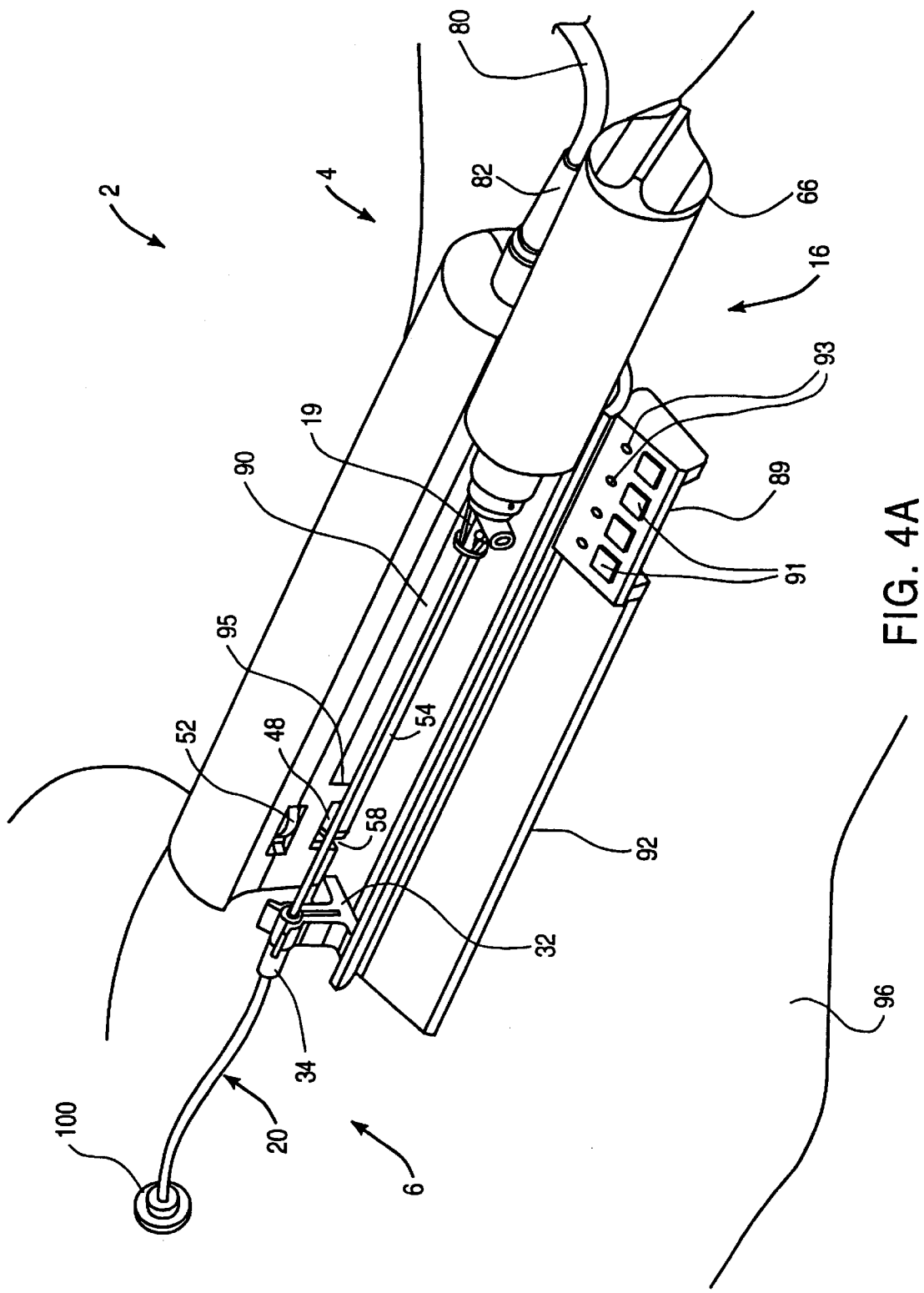
FIG. 4A is an enlarged view of the system of FIG. 4.

FIGS. 1 and 1A illustrate one embodiment of the invention in which a vascular imaging system 2 is shown in partially collapsed and extended conditions, respectively. Vascular imaging system 2 includes broadly a drive assembly 4 and a catheter assembly 6. Assembly 2 is used with an instrument 7, see FIG. 4, which contains all necessary electronics for data interpretation and signal generation, keyboard, monitor, and so forth. Instrument 7 is not part of the invention and thus will not be described in detail.

Drive assembly 4 includes a main body 8 having a generally open first part 10 and a closed second part 12. First part 10 partially houses or cradles the housing 14 of a rotary drive assembly 16. See also FIG. 2. Catheter assembly 6 is mounted to the distal end 18 of housing 14 by a proximal end adapter 19.

As seen in FIGS. 3 and 3A, catheter assembly 6 comprises a hollow sheath 20 defining a longitudinal axis 21 and through which a drive cable 22 extends. Sheath 20 includes a reduced diameter, telescoping poriton 23 which fits within a main sheath portion 25 at one end and extends from distal end 18 of housing 14 at the other. A drive cable 22 (connecting element) has a transducer 24 (operative element), typically an ultrasound transducer, at its distal end 26. The proximal end 28 of drive cable 22 is coupled to a rotary drive motor 30 mounted within housing 14. First part 10 also includes a stationary anchor post 32 adapted to clip onto an anchor post adapter 34 surrounding and secured to the proximal end of main portion 25 of sheath 20. Adapter 34 is used to permit a secure, non-slip connection between anchor post 32 and sheath 20 without collapsing the sheath.

Figure 2:
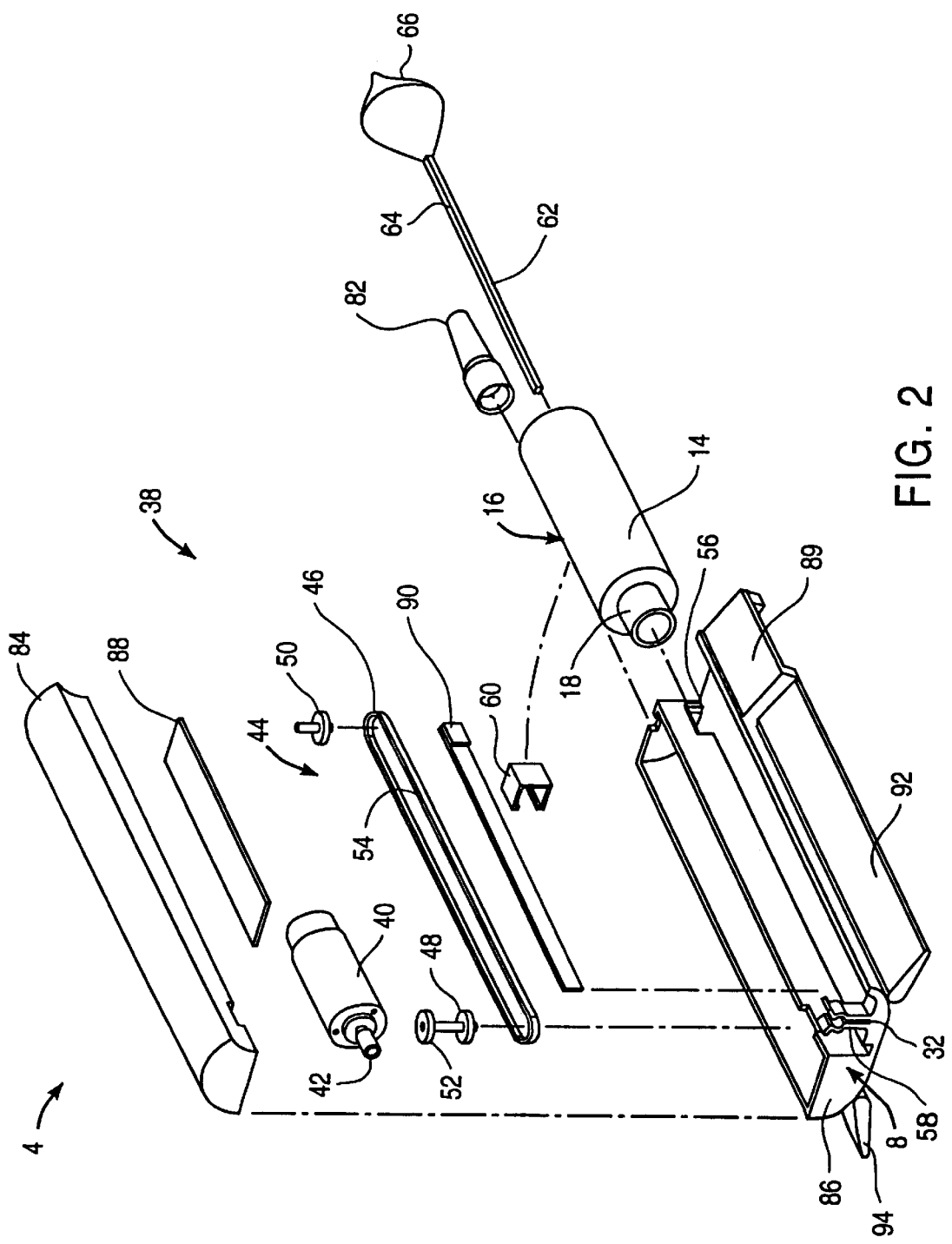
FIG. 2 is an exploded isometric view of the drive assembly of FIG. 1.

The longitudinal movement of rotary drive assembly 16 in the direction of arrow 36 (FIG. 3A) from the partially collapsed condition of FIGS. 1 and 3 to an extended condition shown in FIGS. 1A and 3A is achieved by a longitudinal drive assembly 38 as shown in FIG. 2. Longitudinal drive assembly 38 includes a longitudinal drive motor 40 housed within second part 12. Drive motor 40 includes a drive shaft 42 which drives a drive train 44. Drive train 44 couples drive shaft 42 to housing 14 of rotary drive assembly 16. Drive train 44 includes a drive belt 46 supported at either end by pulleys 48, 50, the pulleys being housed within second part 12. Pulley 48 is directly driven by a drive gear 52, gear 52 being driven by drive shaft 42. The outer reach 54 of drive belt 46 extends through a pair of openings 56, 58 formed in second part 12 (see FIGS. 2 and 4A).

Housing 14 is coupled to outer reach 54 of drive belt 46 through a clutched coupler 60. Clutched coupler 60, shown schematically in FIG. 2, can be clamped to or released from outer reach 54 of belt 46 via manipulation of a clutch actuator 62. Clutch actuator 62 includes an elongate clutch rod 64 and a rotatable clutch handle 66 at the proximal end of the clutch rod. With clutched coupler 60 secured to outer reach 54 of drive belt 46, rotary drive assembly 16 moves in unison with drive belt 46 in a longitudinal direction along longitudinal axis 21.

Housing 14 is maintained adjacent first part 10 by use of appropriately sized and positioned grooves and extensions formed in first part 10 and housing 14. Appropriate stops and/or limit switches can be used to limit the longitudinal movement of assembly 16.

It is desired to minimize the overall length of drive assembly 4. Therefore, it is preferred that clutch actuator 62 remain adjacent to housing 14, such as shown in FIG. 1A, or only spaced apart from housing 14 sufficiently to permit clutch actuator handle 66 to be grasped by the user when housing 14 is fully supported by first part 10 as shown in FIG. 1.

Drive assembly 4 is self-contained with the exception of a power/data cord 80 extending from a strain relief 82, the strain relief being captured between the upper and lower sections 84, 86 of second part 12 as shown in FIG. 2. Power/data cord 80 is used to provide power to the system and to transmit data and instructions to and from system 2. Power/data cord 80 is coupled to a printed circuit board 88 which contains the necessary control circuitry for the system. Printed circuit board 88 is housed within second part 12. Printed circuit board 88 is coupled to a control panel 89 extending from first part 10 adjacent to the proximal end of the first part. Control panel 10 is used to support various start and stop switches 91, indicator lights 93, and so forth. Placement of all such switches and indicators in one place at main body 8, rather than at a location remote from system 2 and the patient, helps to ensure the physician is not distracted during a procedure.

Power and control signals are supplied to rotary drive assembly 16 from printed circuit board 88 through a flexible circuit 90, typically a flat conductor cable. Flexible circuit 90 is coupled to printed circuit board 88 at one end and to rotary drive assembly 16 at the other, flexible circuit 90 having passed through second part 12 at location 95 (see FIG. 4A). The use of a flexible circuit 90 permits the transmission of power and control signals to and data signals from rotary drive assembly 16 even though rotary drive assembly 16 moves along first part 10. Various lines appropriate to the type of operative element used, such as power, data, control, fiberoptics, not shown, pass along drive cable 22 and are typically directly or indirectly coupled to printed circuit board 88 through assembly 16 and circuit 90.

To reduce the weight of rotary drive assembly 16, and thus the torque and power requirements for longitudinal drive motor 40, housing 14 will preferably house only those components that are necessary to move with the housing. Typically this will include rotary drive motor 30 and optionally, a rotary encoder, not shown. Also, patient isolation, to isolate the patient from any high voltages, would typically be carried within housing 14.

Drive assembly 4 also includes a pair of pivotal, adjustable legs 92, 94 extending from main body 8. Legs 92, 94 pivot generally parallel to longitudinal axis 21 to permit main body 8 to rest securely on a patient's leg 96 (see FIGS. 4 and 4A), or other support structure, such as table 98. Legs 92, 94 are preferably pivotally mounted to main body with sufficient frictional resistance to pivoting such that once placed in a position, the adjustable legs stay in that position for proper support of assembly 4. Legs 92, 94 may include a high friction material along their distal edges to help keep drive assembly 4 stable. Legs 92, 94 may also be adjustable in length, articulated along their lengths or both. The provision of legs 92, 94 permits the physician to pay full attention to the procedure and not worry about maintaining drive assembly 4 balanced on the patient's leg, or elsewhere.

An advantage of the disclosed embodiment of the invention is that the drive assembly is always set up to perform one or both of rotary and longitudinal drive functions; no separate setup is needed to perform the longitudinal drive functions as can occur with conventional systems.

In use, a sterile drape (typically a plastic bag) is used to enclose drive assembly 4; main portion 25 of sheath 20 of catheter assembly 6 passes through the otherwise closed end of the sterile drape while the end of power/data cord 80 passes through the opposite end of the sterile drape. Catheter assembly 6 is flushed with saline to eliminate any air bubbles which may otherwise interfere with the operation of transducer 24. Proximal end adapter 19 of catheter assembly 6 is then mounted to distal end 18 of housing 14 of rotary drive assembly 16. With the rotary drive assembly in a partially (or totally) collapsed or extended conditions as suggested in FIGS. 1 and 3 or 1A and 3A, anchor post 32 is clipped onto adapter 34 surrounding the proximal end of main portion 25 of sheath 20. After the distal end of catheter assembly 6 is introduced into the patient through a hemostasis valve 100 (FIG. 4A), and is properly positioned within the patient, drive assembly 4 is stably positioned, typically on the patient's upper leg 96, using legs 92, 94. Rotary drive motor 30 and longitudinal drive motor 40 are then actuated using control panel 89 so that transducer 24 both rotates about longitudinal axis 21 and is pulled longitudinally along the longitudinal axis to generate data sufficient to create a three-dimensional scan or image of the vessel. At the end of the scan, rotary drive assembly 16 can be returned to a desired longitudinal position by the manipulation of clutch actuator handle 66 which temporarily releases clutched coupler 60 from outer reach 54 of drive belt 46. Once in the desired position, actuator handle 66 can be released to permit clutched coupler 60 to reengage outer reach 54 of drive belt 46. Alternatively, motor 40 can be operated in reverse to return assembly 16 to the desired position.

Figure 5:
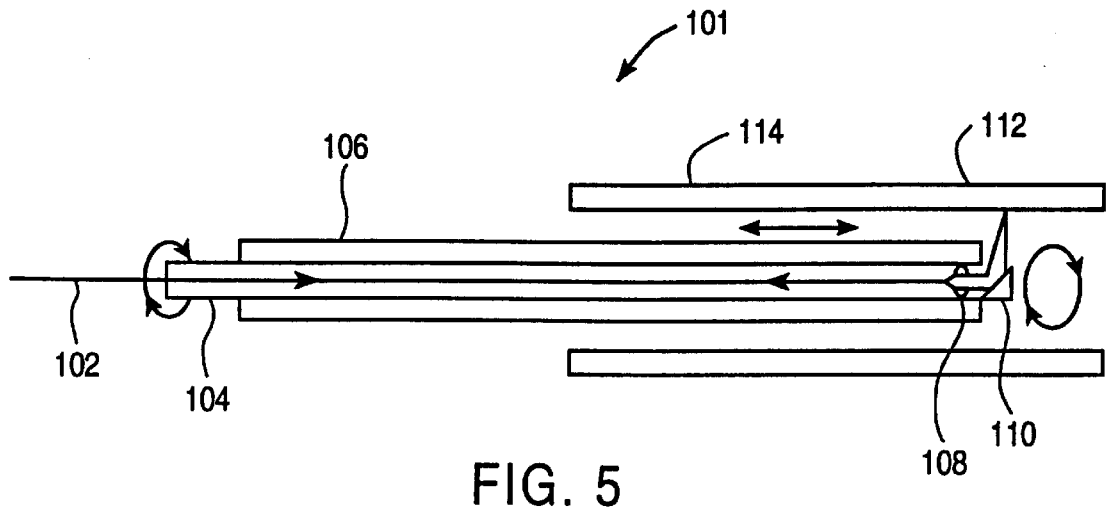
FIGS. 5, 6 and 7 are simplified cross-sectional views of three different types of optical coherence tomography probes which can be utilized in practicing the present invention.

The invention can also be used with optical coherence tomography optical devices which use fiberoptic fibers to create high-resolution images of biological and other structures. FIG. 5 illustrates an optical probe 101 in schematic form, such structure being useful for imaging tubular structures such as blood vessels, the esophagus, or the like. The distal end of an optical fiber 102 is embedded within an inner catheter 104, the inner catheter being rotatably mounted within an outer catheter 106. The inner and outer catheters 104, 106 are both typically housed within a guide sheath, not shown, but corresponding to sheath 20. Outer and inner catheters 104, 106 extend beyond the open distal end of the guide sheath to permit unhindered operation of the optical device. Inner catheter 104 has a lens 108 secured to its outer end. An angled mirror 110 is mounted to the distal end of inner catheter 104 adjacent to lens 108, the angled mirror extending beyond the distal end 112 of outer catheter 106. By rotating inner catheter 104 while simultaneously moving both inner and outer catheters 104, 106 longitudinally, a three-dimensional scan can be obtained of the vessel wall 114. Note that in FIG. 5 inner and outer catheters 104, 106 and optical fiber 102 can be considered to constitute the connecting element corresponding to drive cable 22 of the embodiment discussed above.

Figure 6:
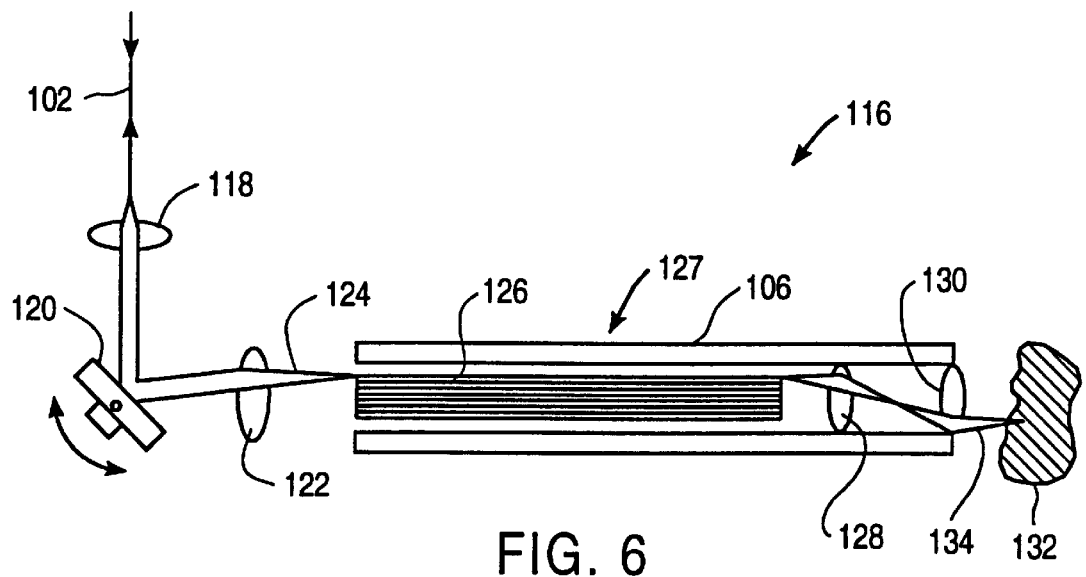

FIG. 6 illustrates a probe 116 having a lens 118 at the distal end of optical fiber 102. Probe 116 also includes a pivotal mirror 120 and a focussing lens 122 which operate to focus a beam 124 to one or more optical fibers in an optical fiber bundle 126. The output from fiber bundle 126 passes through a lens 128 and then a lens 130 before being directed to a sample 132. Fiber bundle 126 and outer catheter 106 constitute a catheter assembly 127. Appropriate movement of mirror 120 permits sample 132 to be scanned by a beam 134. With the embodiment of FIG. 6, outer catheter 106 can be positioned within a hollow sheath corresponding to a sheath 20 and extend from an open distal end of the sheath. Doing so permits outer catheter 106 to be moved longitudinally within the guide sheath according to the present invention. Therefore, catheter assembly 127 corresponds generally to the connecting element which is moved longitudinally according to the invention.

Figure 7:
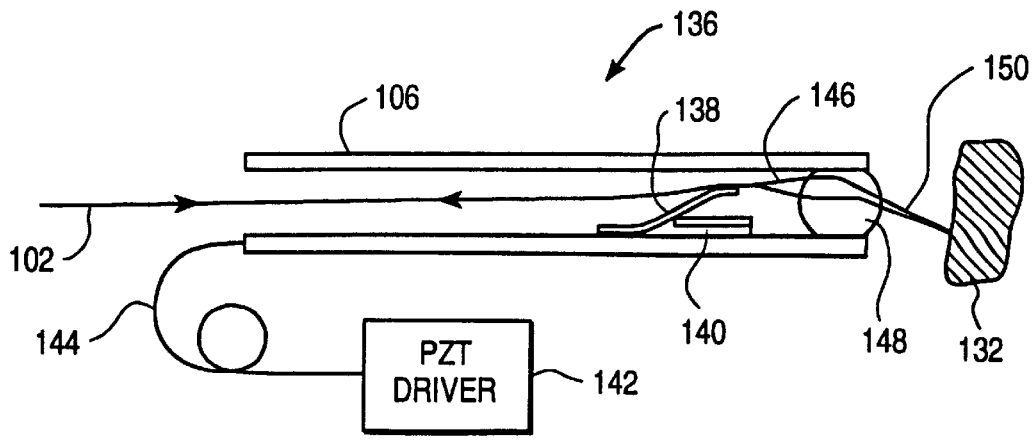

FIG. 7 illustrates a further probe 136. The distal end of optical fiber 102 is connected to a spring 138, the spring mounted to the inner wall of outer catheter 106. Spring 138 rests on and is vibrated by a piezoelectric transducer 140 which is coupled to a piezoelectric driver 142 by a cable 144. Cable 144 extends along the inner wall of outer catheter 106. Energizing transducer 140 causes spring 138 to move causing the transverse movement of the distal end of optical fiber 102. This causes a light beam 146 to move along a graded refractive index lens 148 to cause the output light beam 150 to move or scan across sample 132. As with probe 116, outer catheter 106 could be housed within and extended from the distal end of a sheath so that outer catheter 106 can be driven along the longitudinal axis of the outer sheath.

While there are advantages to separating longitudinal drive motor 40 from rotary drive assembly, housing motor 40 within housing 16 would eliminate much of drive train 44. See FIG. 8 which shows motor 40 driving a drive wheel 154 along first part 10.

All patents referred to above are hereby incorporated by reference.

Modification and variation can be made to the disclosed embodiment without departing from the subject of the invention as defined in the following claims. For example, longitudinal drive assemblies other than those using a drive belt, such as a linear actuator, a worm and worm gear, a rack and pinion, could be used. Legs 92, 94 could be dog-legged or curved so to better engage the patient's leg 96. In some situations it may be possible to eliminate portion 23 of sheath 20. Power could be supplied by batteries and data/instructions could be transmitted using radiofrequency transmitters and receivers so to make system 4 self-contained. While particularly adapted for imaging of vascular regions, the disclosed embodiment of the invention could be modified for diagnostic and therapeutic procedures in vascular and other body structures.

What is claimed is:

1. A catheter system comprising:
   a catheter assembly comprising a hollow sheath having proximal and distal ends, a flexible connecting element housed within the hollow sheath and having proximal and distal ends, an operative element mounted to the connecting element and a proximal end assembly coupled to the proximal end of the connecting element;
   the sheath comprising a distal, main portion and a proximal, telescoping portion, the proximal portion slidable within the main portion; and
   a drive assembly comprising:
      a main body;
      said main body comprising a sheath anchor element secured to said main portion of said sheath;
      a longitudinal drive motor carried by said main body; and
      a longitudinal drive train drivingly coupling the longitudinal drive motor to the proximal end assembly to drive at least a portion of the proximal end assembly longitudinally to move the connecting element longitudinally within the main portion of said sheath.

2. The system according to claim 1 wherein said drive train comprises a drive belt driven by the longitudinal drive motor and a coupler coupling the drive belt to the proximal end assembly.

3. The system according to claim 1 further comprising a support leg extending from said main body.

4. The system according to claim 3 wherein said support leg is an adjustable position support leg.

5. The system according to claim 1 further comprising first and second support legs.

6. The system according to claim 5 wherein said support legs are adjustable support legs.

7. The system according to claim 6 wherein said adjustable support legs are adjustable position support legs.

8. The system according to claim 1 further comprising a power cord, electrically coupled to the longitudinal drive motor, extending from the main body.

9. The system according to claim 1 further comprising a flexible electrical connection electrically coupling the proximal end assembly and the main body.

10. The system according to claim 9 wherein said flexible electrical connection comprises a flat conductor cable.

11. The system according to claim 1 further comprising a control panel carried by the main body and electrically coupled to the longitudinal drive motor.

12. The system according to claim 11 wherein said control panel contains a control element and an indicator.

13. The system according to claim 1 wherein the proximal end assembly comprises a rotary drive assembly.

14. The system according to claim 1 wherein the flexible connecting element comprises a fiberoptic fiber.

15. The system according to claim 14 further comprising a bundle of said fiber optic fibers.

16. The system according to claim 1 wherein the operative element comprises a lens.

17. The system according to claim 1 wherein said connecting element and said operative element constitute a portion of an optical coherence tomography probe.

18. The system according to claim 1 wherein the operative element is selected from a group comprising rotatable ultrasound transducers, phased array ultrasound transducers, fiberoptic devices, optical coherence tomography devices, arterectomy cutters, laser ablation devices and RF energy ablation devices.

19. A catheter system comprising:
   a catheter assembly comprising a hollow sheath having proximal and distal ends, a flexible drive element housed within the hollow sheath and having proximal and distal ends, an operative element mounted to the distal end of the drive element;
   the sheath comprising a distal, main portion and a proximal, telescoping portion, the proximal portion slidable within the main portion; and
   a drive assembly comprising:
      a main body;
      a rotary drive assembly mounted to the main body;
      said rotary drive assembly comprising a rotary drive motor coupled to the proximal end of the drive element;
      said main body comprising a sheath anchor element secured to said main portion of said sheath;
      a longitudinal drive motor carried by said main body; and a longitudinal drive train drivingly coupling the longitudinal drive motor to the rotary drive assembly to drive the rotary drive assembly longitudinally along the main body, whereby the drive element is moved longitudinally within the main portion of said sheath.

20. The system according to claim 19 further comprising first and second adjustable position support legs extending from said main body.

21. The system according to claim 19 further comprising:
  a printed circuit board housed within the main body and electrically coupled to the rotary and longitudinal drive motors;
  a control panel carried by the main body and electrically coupled to the printed circuit board;
  a power cord, electrically coupled to the printed circuit board, extending from the main body; and
  a flexible electrical connection movably electrically coupling the rotary drive motor and the printed circuit board.

22. The system according to claim 19 wherein the operative element is selected from a group comprising rotatable ultrasound transducers, phased array ultrasound transducers, fiberoptic devices, optical coherence tomography devices, arterectomy cutters, laser ablation devices and RF energy ablation devices.

23. A catheter system comprising:
  a catheter assembly comprising a hollow sheath having a proximal end, a flexible connecting element housed within the hollow sheath and having proximal and distal ends, an operative element mounted to the connecting element and a proximal end assembly coupled to the proximal end of the connecting element;
  a drive assembly comprising:
    a main body;
    said main body comprising a sheath anchor element secured to said sheath;
    a longitudinal drive motor carried by said main body; and
    a longitudinal drive train drivingly coupling the longitudinal drive motor to the proximal end assembly to drive at least a portion of the proximal end assembly longitudinally to move the connecting element longitudinally within the sheath;
    wherein the drive train comprises a drive belt driven by the longitudinal drive motor and a clutched coupler coupling the drive belt to the proximal end assembly.

24. The system according to claim 23 wherein said clutched coupler comprises user-operated clutch actuator which allows a user to disengaged said clutch coupler from said drive belt to permit the proximal end assembly to be manually repositioned.

25. A catheter system comprising:
  a catheter assembly comprising a hollow sheath having a proximal end, a flexible connecting element housed within the hollow sheath and having proximal and distal ends, an operative element mounted to the connecting element and a proximal end assembly coupled to the proximal end of the connecting element;
  a drive assembly comprising:
    a main body;
    said main body comprising a sheath anchor element secured to said sheath;
    a longitudinal drive motor carried by said main body; and
    a longitudinal drive train drivingly coupling the longitudinal drive motor to the proximal end assembly to drive at least a portion of the proximal end assembly longitudinally to move the connecting element longitudinally within the sheath;
    wherein said drive train comprises a user-operated clutch allowing a user to manually disengage the proximal end assembly from the longitudinal drive motor.

26. The system according to claim 25 wherein said clutch is carried by the proximal end assembly to move with the proximal end assembly between first and second positions.

27. The system according to claim 26 wherein said clutch comprises a rotatable clutch handle.

28. A catheter system comprising:
  a catheter assembly comprising a hollow sheath having a proximal end, a flexible drive element housed within the hollow sheath and having proximal and distal ends, and an operative element mounted to the distal end of the drive element; and
  a drive assembly comprising:
    a main body;
    a rotary drive assembly mounted to the main body;
    said rotary drive assembly comprising a rotary drive motor coupled to the proximal end of the drive element;
    said main body comprising a sheath anchor element secured to said sheath;
    a longitudinal drive motor carried by said main body; and
    a longitudinal drive train drivingly coupling the longitudinal drive motor to the rotary drive assembly to drive the rotary drive assembly longitudinally along the main body, whereby the drive element is moved longitudinally within the sheath;
    wherein said drive train comprises a drive belt driven by the longitudinal drive motor and a clutched coupler coupling the drive belt to the rotary drive assembly, said clutched coupler comprising user-operated clutch actuator which allows a user to disengage said clutch coupler from said drive belt to permit the rotary drive assembly to be manually repositioned.

29. A catheter system comprising:
  a catheter assembly comprising a hollow sheath having a proximal end, a flexible drive element housed within the hollow sheath and having proximal and distal ends, and an operative element mounted to the distal end of the drive element; and
  a drive assembly comprising:
    a main body;
    a rotary drive assembly mounted to the main body;
    said rotary drive assembly comprising a rotary drive motor coupled to the proximal end of the drive element;
    said main body comprising a sheath anchor element secured to said sheath;
    a longitudinal drive motor carried by said main body; and
    a longitudinal drive train drivingly coupling the longitudinal drive motor to the rotary drive assembly to drive the rotary drive assembly longitudinally along the main body, whereby the drive element is moved longitudinally within the sheath;
    wherein said drive train comprises a user-operated clutch allowing a user to manually disengage the rotary drive assembly from the longitudinal drive motor, said clutch being carried by the rotary drive assembly to move with the rotary drive assembly between first and second positions.

30. A catheter system drive assembly comprising:

a main body;

a rotary drive assembly mounted to the main body;

said rotary drive assembly comprising a rotary drive motor coupleable to a catheter drive element;

said main body comprising a catheter sheath anchor element;

a longitudinal drive motor carried by said main body; and a longitudinal drive train drivingly coupling the longitudinal drive motor to the rotary drive assembly to drive the rotary drive assembly longitudinally along the main body;

wherein said drive train comprises a drive belt driven by the longitudinal drive motor and a coupler coupling the drive belt to the rotary drive assembly.

31. The drive assembly according to claim 30 wherein said coupler is a clutched coupler.

32. The drive assembly according to claim 31 wherein said clutched coupler comprises user-operated clutch actuator which allows a user to disengaged said clutch coupler from said drive belt to permit the rotary drive assembly to be manually repositioned.

33. A catheter system drive assembly comprising:

a main body;

a rotary drive assembly mounted to the main body;

said rotary drive assembly comprising a rotary drive motor coupleable to a catheter drive element;

said main body comprising a catheter sheath anchor element;

a longitudinal drive motor carried by said main body; and a longitudinal drive train drivingly coupling the longitudinal drive motor to the rotary drive assembly to drive the rotary drive assembly longitudinally along the main body;

wherein said drive train comprises a user-operated clutch allowing a user to manually disengage the rotary drive assembly from the longitudinal drive motor.

34. The drive assembly according to claim 33 wherein said clutch is carried by the rotary drive assembly to move with the rotary drive assembly between first and second positions.

35. The drive assembly according to claim 34 wherein said clutch comprises a rotatable clutch handle.

* * * * *